United States Patent

Engel et al.

[11] Patent Number: 4,923,858
[45] Date of Patent: May 8, 1990

[54] SUBSTITUTED 3-(N-HETEROCYCLIC)-2,6-DIAMINOPYRIDINES AND -N-OXIDES

[75] Inventors: Jürgen Engel, Alzenau; Peter Emig, Niederdorfelden; Bernd Nickel, Mühltal; Istvan Szelenyi, Schwaig, all of Fed. Rep. of Germany

[73] Assignee: Asta Pharma Aktiengesellschaft, Frankfurt am Main, Fed. Rep. of Germany

[21] Appl. No.: 352,287

[22] Filed: May 16, 1989

[30] Foreign Application Priority Data

May 16, 1988 [DE] Fed. Rep. of Germany ....... 3816629

[51] Int. Cl.$^5$ .................... A61K 31/44; C07D 401/04; C07D 413/04; C07D 417/04
[52] U.S. Cl. ................................ 514/211; 514/218; 514/227.2; 514/228.8; 514/256; 514/340; 514/341; 514/342; 540/488; 540/492; 544/54; 544/96; 544/316; 546/278; 546/280; 546/275
[58] Field of Search ....................... 546/275, 278, 280; 514/340, 341, 342, 211, 218, 227.2, 228.8, 256; 540/488, 492; 544/54, 96, 316

[56] References Cited

FOREIGN PATENT DOCUMENTS 698384  5/1967  Belgium .
736139  1/1969  Belgium .
764362  3/1971  Belgium .

*Primary Examiner*—Richard A. Schwartz
*Assistant Examiner*—Jacqueline Haley
*Attorney, Agent, or Firm*—Cushman, Darby & Cushman

[57] ABSTRACT

Compounds of the general formula:

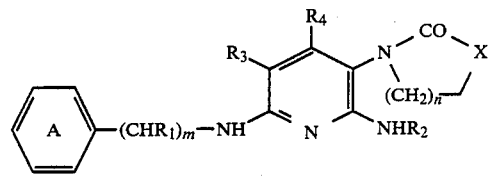

wherein the radicals $R_1$ and $R_2$ are the same or different and represent hydrogen or $C_1$–$C_6$-alkyl, the radicals $R_3$ and $R_4$ are the same or different and represent hydrogen, $C_1$–$C_6$-alkyl, hydroxy, $C_1$–$C_6$-alkoxy, $C_2$–$C_6$-alkanoyloxy, halogen or $C_2$–$C_6$-alkanoyl, X is oxygen, sulphur or the group —$NR_5$ and $R_5$ is hydrogen, $C_1$–$C_6$-alkyl, $C_2$–$C_6$-alkanoyl or benzoyl, m and n in each case may represent the integers 1, 2 or 3 and the phenyl radical A is unsubsituted or is substituted by halogen, nitro, $C_1$–$C_6$-alkyl, trifluoromethyl, $C_3$–$C_7$-cycloalkyl, hydroxy, $C_1$–$C_6$-alkoxy, $C_2$–$C_6$-alkanoyloxy, amino, $C_1$–$C_6$-alkylamino, di-$C_1$–$C_6$-alkylamino, $C_2$–$C_6$-alkanoylamino, CN, carboxy, $C_1$–$C_6$-alkoxycarbonyl, phenyl, $C_1$–$C_6$-alkylphenyl or trifluoromethylphenyl, their pyridine-N-oxides and physiologically acceptable salts thereof, processes for their preparation and medicines containing such compounds as active ingredients.

3 Claims, No Drawings

SUBSTITUTED 3-(N-HETEROCYCLIC)-2,6-DIAMINOPYRIDINES AND -N-OXIDES

The present invention relates to novel pharmaceutically active pyridine compounds, a method for their preparation, and their use in medicines.

BACKGROUND OF THE INVENTION

Compounds having the following formula are known from Belgian Pat. Nos. 698 384 and 764 362:

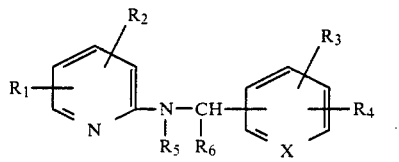

In this formula, one or more of the radicals $R_1$ to $R_4$ represent amino groups which may be acylated or alkylated by low molecular weight radicals, and, where the radicals $R_1$ to $R_4$ do not represent amino groups, then they represent hydrogen or halogen atoms, low molecular weight alkyl-, trifluoromethyl-, cyano-, thiocyano-, mercapto-, low molecular weight alkylthio-, acylthio-, hydroxy-, methylenedioxy-, low molecular weight alkoxy-, acyloxy-, nitro-, carboxy-, carbalkoxy- or carbamoyl groups, $R_5$ represents a hydrogen atom or an acyl radical, $R_6$ represents a hydrogen atom, a low molecular alkyl- or an aralkyl group and X represents a nitrogen weight atom or the CH group and wherein the acyl radicals are derived from carbonic acid, carbonic acid semi-morpholid, from carbonic acid monoesters, preferably from, substituted benzoic acids and pyridine carboxylic acids or from saturated or unsaturated, low molecular weight aliphatic mono- or dicarboxylic acids optionally substituted by a morpholino radical.

The compounds possess anti-inflammatory and analgesic action, the analgesic effect being specifically an analgesic action on the central nervous system, that is an action within the nerve cells of the spinal cord and/or the nerve cells of the brain.

SUMMARY OF THE INVENTION

The present invention relates to new triamino pyridines having a heterocyclic radical in the 3-position. More specifically, the present invention relates to compounds of the general formula:

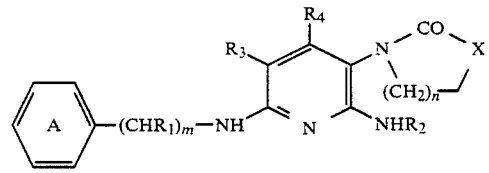

wherein the radicals $R_1$ and $R_2$ are the same or different and represent hydrogen or $C_1-C_6$-alkyl, the radicals $R_3$ and $R_4$ are the same or different and represent hydrogen, $C_1-C_6$-alkyl, hydroxy, $C_1-C_6$-alkoxy, $C_2-C_6$-alkanoyloxy, halogen or $C_2-C_6$-alkanoyl, X is oxygen, sulphur or the group —$NR_5$ and $R_5$ is hydrogen, $C_1-C_6$-alkyl, $C_2-C_6$-alkanoyl or benzoyl, m and n in each case may represent the integers 1, 2 or 3 and the phenyl radical A is unsubstituted or is substituted by halogen, nitro, $C_1-C_6$-alkyl, trifluoromethyl, $C_3-C_7$-cycloalkyl, hydroxy, $C_1-C_6$-alkoxy, $C_2-C_6$-alkanoyloxy, amino, $C_1-C_6$-alkylamino, di-$C_1-C_6$-alkylamino, $C_2-C_6$-alkanoylamino, CN, carboxy, $C_1-C_6$-alkoxycarbonyl, phenyl, $C_1-C_6$-alkylphenyl or trifluoromethylphenyl, their pyridine-N-oxides and physiologically acceptable salts thereof according to Formula I. These compounds have improved properties. The compounds of the invention are pharmacologically active. They have a pronounced anti-convulsive and anti-epileptic effect.

Particularly advantageous is the extended therapeutic range. It should particularly be noted that the incidence of side effects (such as sedation, ataxia, alcohol-enhancing effect) is extremely low at the effective anti-convulsive, anti-epileptic and peripheral analgesic doses.

Some compounds also have, in addition, a specific peripheral analgesic effect (effect on the peripheral nervous system) as well as an anti-inflammatory effect. It is therefore an object of the invention to provide compounds having favorable pharmacological properties which can, for example, be employed as medicines with an anti-convulsant action.

The following description relates to preferred features of the invention:

Alkyl, alkoxy or alkanoyl groups present in Formula I may be straight or branched. The same applies to the alkyl and alkoxy groups, should these be a component of other groups present (for example in the form of monoalkyl- or dialkylamino groups, alkanoylamino groups, alkanoyloxy groups, alkoxycarbonyl groups and the like). The halogen atoms are chlorine, bromine or fluorine, in particular chlorine and fluorine. The alkyl and alkoxy groups, as such or as components of other composite groups, contain in particular 1-4 carbon atoms, preferably 1 or 2 carbon atoms. Alkanoyl groups, alkanoyloxy groups or alkanoyl amino groups contain in particular of 2-4, preferably 2-3 carbon atoms. The $C_3-C_7$-cycloalkyl group has 5 or 6 carbon atoms. X preferably represents oxygen or the group —$NR_5$.

Particularly advantageous properties are displayed by those compounds of Formula I in which X is oxygen, the radicals $R_1$, $R_2$, $R_3$ and $R_4$ are hydrogen and m is the integer 1, n is 1 or 2 and the phenyl ring A preferably contains one of the substituents listed, such a substituent preferably containing a halogen atom (for example fluorine, chlorine) or the trifluoromethyl group. If the phenyl ring A contains a substituent, this is preferably in the 4-position, although substitution in the 2- and/or 3-position is also possible. The phenyl radical A may, however, also contain 2, 3, 4 or 5 of the above mentioned substituents and these substituents may be the same or different.

If the phenyl radical A is substituted by a trifluoromethylphenyl radical, this is in particular the 4-trifluoromethylphenyl radical. The same applies in the event that the phenyl ring A is substituted by a $C_1-C_6$-alkylphenyl radical. The $C_1-C_6$-alkyl radical in this case is preferably methyl or ethyl.

The present invention also provides a process for the preparation of compounds of the general formula:

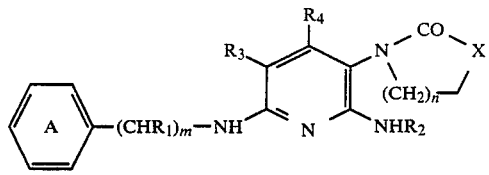

wherein the radicals $R_1$ and $R_2$ are the same or different and represent hydrogen or $C_1$-$C_6$-alkyl, the radicals $R_3$ and $R_4$ are the same or different and represent hydrogen, $C_1$-$C_6$-alkyl, hydroxy, $C_1$-$C_6$-alkoxy, $C_2$-$C_6$-alkanoyloxy, halogen or $C_2$-$C_6$-alkanoyl, X is oxygen, sulphur or the group —$NR_5$ and $R_5$ is hydrogen, $C_1$-$C_6$-alkyl, $C_2$-$C_6$-alkanoyl or benzoyl, m and n in each case may represent the integers 1, 2 or 3 and the phenyl radical A is unsubstituted or is substituted by halogen, nitro, $C_1$-$C_6$-alkyl, trifluoromethyl, $C_3$-$C_7$-cycloalkyl, hydroxy, $C_1$-$C_6$-alkoxy, $C_2$-$C_6$-alkanoyloxy, amino, $C_1$-$C_6$-alkylamino, di-$C_1$-$C_6$-alkylamino, $C_2$-$C_6$-alkanoylamino, CN, carboxy, $C_1$-$C_6$-alkoxycarbonyl, phenyl, $C_1$-$C_6$-alkylphenyl or trifluoromethylphenyl, their pyridine-N-oxides and physiologically acceptable salts thereof. The method is carried out with a starting material having the formula:

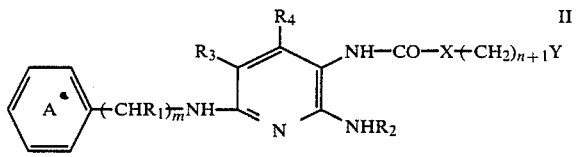

wherein $R_1$, $R_2$, $R_3$, $R_4$, X and n have the meanings given and Y represents a hydroxy group esterified by a strong inorganic or organic acid. This compound is cyclized with splitting off of HY, optionally present free hydroxy groups and/or amino groups are acylated and or oxidized to the corresponding pyridine-N-oxide and the so-obtained compounds are optionally converted into their salts.

The process for the preparation of compounds of Formula I from compounds of Formula II is carried out in a solvent or dispersing agent or also without solvent at temperatures between 0° and 220° C. If a solvent or dispersing agent is used, a temperature range between 0° and 100° C., in particular between 5° and 60° C. or also between 10° and 50° C. may be used. If there is no solvent, the reaction occurs for example between 150° and 220° C., preferably between 160° to 190° C. If n=2, the process is generally carried out at temperatures between 20° and 70° C., preferably 40°-50° C.; if n=1 it is generally carried out at temperatures between 10° and 40°, preferably 10°-30, in particular 20°-25° C.

The esterified hydroxy group (represented by Y) is a reactive ester. In this case the reactive ester may be that of a strong organic or inorganic acid especially for example a halohydric acid, for example hydrochloric, hydrobromic or hydroiodic acid, or a sulphonic acid such as an aryl or $C_1$-$C_6$-alkylsulphonic acid, for example of lower alkylbenzene sulphonic acids (p-toluene sulphonic acid). Y is in particular halogen (Cl, Br, I).

Solvents or dispersing agents which may, for example, be used are: lower aliphatic alcohols (1-6 carbon atoms such as methanol, ethanol, propanol, isopropanol, butanol), lower aliphatic ethers (diethylether, diisopropylether), aromatic hydrocarbons (benzene, toluene, xylene), cyclic ethers (dioxane, tetrahydrofuran), esters of lower aliphatic carboxylic acids with lower aliphatic alcohols, amides and N-alkyl-substituted amides of aliphatic $C_1$-$C_4$-carboxylic acids (dimethyl formamide, dimethylacetamide), $C_1$-$C_6$-dialkylsulphones (dimethylsulphone, tetramethylenesulphone), $C_1$-$C_6$-dialkylsulphoxides (dimethylsulphoxide) as well as other aprotic agents such as N-methylpyrrolidone, tetramethylurea, hexamethyl phosphoric acid triamide, acetonitrile.

The individual alkyl radicals of the above listed solvents contain for example 1-6, in particular 1-4 carbon atoms.

The process is optionally carried out in the presence of condensing agents. Condensing agents of this type that may, for example, be considered are: inorganic condensing agents such as ammonia, alkaline metal or alkaline earth metal hydroxides (NaOH, KOH), alkali metal hydrides, alkali metal amides, alkali metal or alkaline earth metal carbonates or organic bases such as pyridine, tertiary amines, piperidine, alkali metal alcoholates, alkali metal acetates or also triethylphosphate. The alkali metals are in particular sodium or potassium. The process may also be carried out under phase-transfer conditions (that is with addition of one or more long-chain amines such as a benzyltributyl ammonium halide, a tetrabutylammonium halide or benzyltriphenyl phosphonium chloride).

It is also possible to use a starting component of Formula II which contains a conventional amino protecting group, in place of the radical $R_2$, which may easily be split off solvolytically or by hydrogenation after completion of the reaction.

The starting material of Formula II is preferably used in the form of its salt with an inorganic acid (for example as the hydrochloride).

The starting materials of Formula II may for example be obtained as follows:

In compounds having the formula:

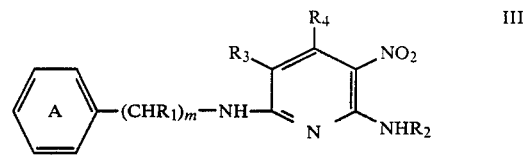

which are known or which may be obtained in analogous manner to the corresponding known compounds (see Belgian Pat. Nos. 698,384; 764,362; 736,139; published German Patent Specification DOS No. 33 37 593) the nitro group in the 3-position is reduced in the manner known for this purpose (for example as set out in the above listed patent specifications for the reduction of the nitro group in the 3-position of a pyridine ring) and the compound of Formula III so obtained with the amino group in the 3-position is reacted in a conventional manner for example with a compound of the formula $$Hal^1-CO-X(CH_2)_n-Hal^2 \qquad IV$$

or the formula $$Hal^1-CO-X(CH_2)_n-OH \qquad V.$$

wherein X and n have the meanings given above and $Hal^1$ and $Hal^2$ are the same or different and represent chlorine, bromine or iodine.

In place of the compounds IV and V, it is also possible to use corresponding equivalent compounds which are capable of replacing a hydrogen atom of the amino group in the 3-position obtained by means of the reduction by the acyl group —CO—X—(CH$_2$)$_n$—Y. Acylation of the amino group in the 3-position is conveniently effected immediately after reduction of the nitro group in the reaction mixture present. This conversion may for example be carried out at temperatures between −10° and 100° C., preferably 0° and 60° C. Suspending agents or solvents which may for example be used for this conversion are: saturated alicyclic and cyclic ethers (dioxane, tetrahydrofuran, lower dialkyl ethers such as diethyl ether, diisopropyl ether), lower alkanols such as ethanol, isopropanol, butanol, lower aliphatic ketones (acetone, methylethyl ketone), lower aliphatic hydrocarbons or hydrogen halides (methylene chloride, chloroform, 1,2-dichloroethane), aromatic hydrocarbons (benzene, toluene, xylene), lower dialkyl amides of lower saturated aliphatic carboxylic acids (dimethylformamide, dimethylacetamide), tetramethylurea, N-methylpyrrolidone, dimethylsulphoxide or mixtures of these solvents.

In general the reactive components are reacted in molar amounts. It may, however, optionally be appropriate to use a slight excess of a reactive component. The conversion may optionally also be carried out in the presence of basic or acid-binding agents, such as alkali metal bicarbonates (potash, soda), alkali metal carbonates, alkali metal acetates, alkali metal hydroxides, tertiary amines (for example triethylamine) or basic ion exchangers.

The latter applies in particular if haloformic acid ester derivatives are used. The process may, however, also be carried out without basic condensing agents or acid binding agents with the compound of Formula II serving as acid binding agent, the HCl salt of the desired compound thus being formed.

Should the starting materials of Formula III not be known, such starting materials may for example be obtained by reaction of 3-nitropyridines of formula:

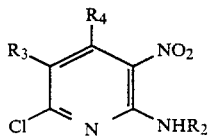

with amines of the formula

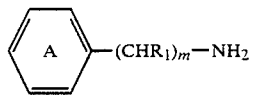

with or without solvents, at temperatures of from 0° to 200° C. optionally in the presence of an additional hydrochloric acid acceptor by analogy with Belgian Pat. Nos. 698 384, 764 362 or 736 139 or according to German Pat. No. 1 795 797. The above mentioned 3-nitropyridines may for example be obtained from the corresponding 2,6-dichloropyridines (with the radicals R$_3$ and R$_4$) by a conventional nitration and subsequent amination with an amine of formula R$_2$—NH$_2$ (replacement of the Cl in 2-position).

The 2,6-dichloropyridines may for example be obtained in conventional manner by treatment of pyridines of formula:

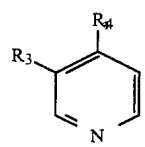

with chlorinating agents (thionyl chloride, sulphuryl chloride, phosphorus trichloride, phosphorus oxytrichloride, phosphorus pentachloride, HCl). Free hydroxy groups present are in this case optionally protected by conventional protecting groups which are optionally split off after the chlorination.

Starting compounds of Formula II in which Y is an esterified hydroxy group may also be obtained from such starting substances of Formula II in which Y is a hydroxy group, by reaction with thionylhalides (chlorides, bromides, iodides) or equivalent agents in halogenated hydrocarbons (chloroform) or aromatic hydrocarbons (benzene) or in pyridine at temperatures between 20° and 150° C. (preferably at the reflux temperature of the solvent used). Starting materials of Formula II in which Y is a hydroxy group which is esterified by another acid such as a hydrogen halide (where Y is therefore for example an alkylsulphonyloxy group or an arylsulphonyloxy group) may for example be obtained from the corresponding hydroxy compounds (Y=OH) by reaction with C$_1$–C$_6$-alkyl-sulphonic acid chlorides or the corresponding arylsulphonic acid chlorides in the inert solvents conventionally used therefor (benzene, toluene, xylene, chloroform, methylene chloride, dioxane) at temperatures between 20°–150° C. The reaction is preferably carried out in the presence of an acid-binding substance (for example tertiary amines such as triethylamine).

If R$_2$ is hydrogen, the amino group may be protected by an protecting group that is easily split off; the same applies by analogy for other optionally present amino groups and/or hydroxy groups.

Products of the process of Formula I which contain free hydroxy groups, amino groups or where X is the group —NR$_5$, in which R$_5$ stands for hydrogen, may be acylated to these groups. This involves the introduction of C$_2$-C$_6$-alkanoyl groups, C$_1$-C$_6$-alkoxycarbonyl groups or also the introduction of a benzoyl group (should X be for example the group —NR$_5$ and R$_5$ be benzoyl). This acylation may take place in inert solvents or suspending agents at temperatures between 0° to 200° C., preferably 20° to 150° C. Solvents or dispersing agents which may, for example, be employed are: aromatic hydrocarbons such as for example benzene, toluene, xylene; aliphatic ketones such as for example acetone, methylethylketone; halogenated hydrocarbons such as for example chloroform, carbon tetrachloride, chlorobenzene, methylene chloride; aliphatic ethers such as for example butyl ethers; cyclic ethers such as for example tetrahydrofuran, dioxane; sulphoxides such as for example dimethylsulphoxide; tertiary acid amides such as dimethyl formamide, dimethylacetamide, N-methylpyrrolidone, hexamethylphosphoric acid triamide; aliphatic alcohols such as methanol, ethanol, isopropanol, amylalcohol, tert.-butanol, cycloaliphatic hydrocarbons such as cyclohexane and the like. It is also possible to use aqueous mixtures of the above mentioned solvents. The reaction is often carried out at the reflux temperature of the solvents or dispersing agents used.

Acylating agents that may be used are: ketenes as well as acid halides (chlorides, bromides, iodides), acid anhydrides or acid esters of aliphatic carboxylic acids with 2-6 carbon atoms or $C_1$-$C_6$-alkoxycarbonyl halides (chlorides, bromides).

Solvents or suspending agents which may for example be used are: water, lower aliphatic alcohols, cyclic ethers such as dioxane or tetrahydrofuran, aliphatic ethers, dimethylformamide and the like as well as mixtures of these agents.

It is possible to optionally add acid binding agents such as alkali metal carbonates, alkali metal hydroxides, alkali metal alcoholates or a tertiary amine, for example triethylamine or pyridine. Pyridine may simultaneously be used as solvent. The above mentioned esters are in particular those of the above mentioned carboxylic acids with lower aliphatic alcohols. The acylation may also be conducted in such a way that an alkali metal compound is first prepared from the compound to be reacted by reacting it in an inert solvent such as dioxane, dimethylformamide, benzene or toluene with an alkali metal, alkali metal hydride or alkali metal amide (in particular sodium or sodium compounds) at temperatures between 0° and 150° C. and then adding the acylating agent.

In place of the acylating agent mentioned it is also possible to use other chemically equivalent agents conventionally used in chemistry (see for example also L. F. and Mary Fieser "Reagents for Organic Synthesis", John Wiley and Sons, Inc., New York, 1967, Vol. 1, pages 1303-4 and Vol. 2, page 471).

These acyl groups in the compounds of Formula I may be split off again solvolytically. This solvolytic splitting off occurs for example by saponification with dilute acids or by means of basic substances (potash, soda, aqueous alkali solutions, alcoholic alkali solutions, $NH_3$) at temperatures between 10° and 150° C., in particular 20° to 100° C. Solvents or suspending agents which may for example be used for this purpose are: water, lower aliphatic alcohols, cyclic ethers such as dioxane or tetrahydrofuran, aliphatic ethers, dimethylformamide and so on as well as mixtures of these agents.

The conversion of compounds of Formula I into the pyridine-N-oxides may for example be carried out in solvents such as lower alcohols (methanol, ethanol), chloroform or other chlorinated hydrocarbons, benzene, toluene, acetone, dilute acetic acid, ethyl acetate or lower aliphatic acid anhydrides (for example acetic anhydride) with hydrogen peroxide, a conventional aliphatic or aromatic peracid (peracetic acid, peroxybenzoic acid, peroxy m-chlorobenzoic acid or other monosubstitution products of hydrogen peroxide such as alkali metal peroxides or alkyl peroxides (for example tert.-butylperoxide) at temperatures between 0° and 150° C., preferably 0° to 100° C.

The compounds of the general Formula I obtained in pure form are present in the form of bases and may optionally be converted into therapeutically usable salts by reaction with acids.

Acids of this type that may for example be mentioned are: hydrohalic acids, sulphuric acid, phosphoric acids, nitric acid, perchloric acid, organic mono-, di- or tricarboxylic acids of the aliphatic, alicyclic, aromatic or heterocyclic series as well as sulphonic acids. Examples thereof are: formic, acetic, propionic, succinic, glycollic, lactic, malic, tartaric, citric, ascorbic, maleic, fumaric, hydroxymaleic, gluconic or pyruvic acid; phenylacetic, benzoic, p-aminosalicylic acid, embonic acid, methanesulphonic, ethanesulphonic, hydroxyethanesulphonic, ethylenesulphonic acid; halogenbenzenesulphonic, toluenesulphonic, naphthalinesulphonic acid or sulphanilic acid or also 8-chlorotheophylline.

In the maximum electro-shock test, the compounds of the invention display a good anti-epileptic effect. For example in the above named experimental method, an anti-epileptic effect is obtained in 50% of the animals with a dosage of 56 mg/body weight mouse.

The minimum effective dose in the above mentioned animal experiment is for example
20 mg/kg orally
5 mg/kg intravenously The general dosage range for this effect (animal experiment as above) may for example be:
20-100 mg/kg oral, in particular 40-80 mg/kg mouse
5-25 mg/kg intravenous, in particular
10-20 mg/kg mouse The general profile of action of the compounds of the invention is comparable to the effect of the known pharmaceutically active substance phenytoin or carbamazepine. However, the compounds of the invention possess for example a greater therapeutic range.

Indications which may be considered for the compounds of the invention are: epilepsy.

In general, the dosage units contain between 20 to 200, preferably 50 to 100 mg of the active component(s) of the invention.

Administration may for example be in the form of tablets, capsules, pills, coated tablets, suppositories, ointments, gels, creams, powder, dusting powder, aerosols or in liquid form. Liquid forms of application that may for example be used are: oily or alcoholic or aqueous solutions as well as suspensions and emulsions. Preferred forms of application are tablets containing between 50 and 100 mg or solutions which contain between 1.5 to 5 percent by weight of active substance.

The individual dosage of the active component of the invention may for example be
(a) in the case of oral medicinal forms between 20 and 400 mg, preferably 100 mg
(b) in the case of parenteral medicinal forms (for example intravenous, intramuscular) between 5 and 40 mg, preferably 20 mg
(c) in the case of medicinal forms for rectal application between 20 and 400 mg, preferably 100 mg
the doses are in each case calculated for the free base form.

It is for example possible to recommend 1 to 2 tablets containing 50 to 100 mg of active substance 3 times daily or for example in the case of intravenous injection one ampoule containing 2 to 5 ml with 10 to 20 mg of substance 1 to 2 times daily. In the case of oral administration the minimum daily dosage is for example 150; the maximum daily dosage in the case of oral administration should not exceed 600.

For the treatment of dogs and cats the oral single dose is generally between about 10 and 20 mg/kg body weight; the parenteral dose about between 2 and 10 mg/kg body weight. The acute toxicity of the compounds of the invention in the mouse (expressed as LD50 mg/kg); method after Miller and Tainter: Proc. Soc. Exper. Biol. a. Med. 57 (1944) 261) is for example between 1000 and 1500 mg/kg (or above 1200 mg/kg) in the case of oral administration.

The medicines may be used in human medicine, veterinary medicine as well as in agriculture alone or mixed with other pharmacologically active substances.

DETAILED DESCRIPTION OF PREFERRED EMBODIMENTS

The following examples illustrate the invention.

EXAMPLE 1

2-Amino-3-(oxazolidin-2-one-3-yl)-6-(4-fluorobenzylamino)-pyridine

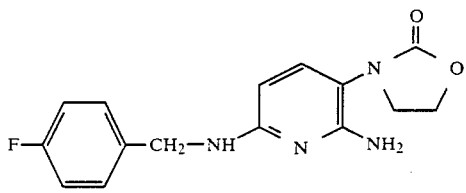

A suspension of 50 g (0.12 Mol) of 2-amino-3-[(2-bromethoxy)-carbonylamino]-6-(4-fluoro-benzylamino)-pyridine hydrochloride in 200 ml of methanol is added to 250 ml of 10% ethanolic ammonia and the mixture is stirred for a total of 24 hours at room temperature under argon (with a further 100 ml of 10% ethanolic ammonia being added after 12 hours). The resultant crystalline compound is filtered under suction and dried in a vacuum at room temperature.

Melting point: 176° C.
Yield: 21.6 g.

The compound may also be prepared as follows:

Sodium hydroxide solution (2N) is added to a suspension of 50 g of 2-amino-3-[(2-bromethoxy)-carbonylamino]-6-(4-fluorobenzylamino)-pyridine hydrochloride in 200 ml of methanol until the pH reaches 10.5, the pH again being adjusted to a pH of 10.5 after about 30 minutes by means of further addition of 2N sodium hydroxide solution.

To form the hydrochloride, 21.6 g of 2-amino-3-(oxazolidin-2-one-3-yl)-6-(4-fluoro-benzylamino)-pyridine are dissolved in cold acetone in an atmosphere of argon and adjusted to a pH of 4 with 5.5N isopropanolic hydrochloric acid. The crystalline 2-amino-3-(oxazolidin-2-one-3-yl)-6-(4-fluoro-benzylamino)-pyridine hydrochloride precipitates out after about 15 minutes. The product is suction filtered, washed with ice-cold acetone and dried in a vacuum at room temperature.

Melting point: 220° C.
Yield: 23.4 g (97% of theory).

The starting material used may for example be prepared as follows:

20 g of 2-amino-3-nitro-6-(4-fluoro-benzylamino)-pyridine are suspended with 15.6 g of Raney nickel and 15.6 g of magnesium sulphate (anhydrous) in 215 mg of dioxane and hydrogenated at 5 bar and 60° C. for 2.5 hours. The reaction product is cooled to 25° C., the Raney nickel and the magnesium sulphate are suction filtered off and reacted with 17.1 g of chloroformic acid-2-bromoethyl ester. The precipitated, crystalline 2-amino-3-[(2-bromoethoxy)carbonylamino]-6-(4-fluoro-benzylamino)pyridine hydrochloride is washed with a little ice-cold isopropanol and with ether and is dried in a vacuum at room temperature.

Melting point of the hydrochloride: 216° C.
Yield: 25 g.

By analogy with Example 1 the compounds listed in Table 1 of the following formula are prepared from the corresponding starting materials II:

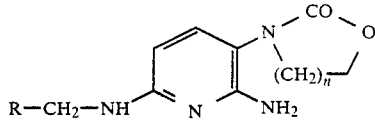

TABLE 1

Amount of ethanolic ammonia (in all in each case 60 ml; amount of solvent (methanol) in each case 35 ml).

| Example No. | R | n | Yield % | MP °C. (hydrochloride) | Starting material II (as HCl salt) Mol | MP °C. |
|---|---|---|---|---|---|---|
| 2 | 2,4,6-trimethylphenyl (H3C-, CH3, CH3) | 1 | 65,3 | 210 | 0,015 | 215 (dis.) |
| 3 | phenyl | 1 | 63,3 | 186 | 0,037 | 219 (dis.) |
| 4 | 4-chlorophenyl (Cl-) | 1 | 73,7 | 201 | 0,029 | 205 (dis.) |
| 5 | 4-trifluoromethylphenyl (F3C-) | 1 | 77,3 | 221 | 0,017 | 206 (dis.) |

TABLE 1-continued

Amount of ethanolic ammonia (in all in each case 60 ml; amount of solvent (methanol) in each case 35 ml).

| Example No. | R | n | Yield % | MP °C. (hydrochloride) | Starting material II (as HCl salt) Mol | MP °C. |
|---|---|---|---|---|---|---|
| 6 | phenyl | 2 | 64,2 | 237 | 0,021 | 220 (dis.) |
| 7 | F-phenyl | 2 | 68,5 | 254 | 0,02 | 220 (dis.) |

Dis. = disintegration

EXAMPLES OF GALENIC FORMULATIONS

Capsules with 100 mg of active substance 10 kg of compound according to Example 1 (hydrochloride) are granulated in known manner in a fluidized air bed spray granulating apparatus with a solution of 0.25 kg of gelatin in 2.25 kg of water. After addition of 0.80 kg of corn starch, 0.1 kg of magnesium stearate and 0.05 kg of highly disperse silicon dioxide with mixing, the mixture is filled in amounts of, in each case, 112 mg into size 3 hard gelatin capsules.

Each capsule contains 100 mg of active substance.

Suppositories containing 150 mg of active substance 1.5 kg of compound according to Example 1 (hydrochloride) are suspended in 19 kg of melted hard fat[1]. After homogenization the suspension is cast in hollow molds of 2.3 ml each in the conventional manner and cooled. Each suppository weighing 2.05 g contains 150 mg of active substance.

[1] Hard fat is a mixture of mono-, di- and triglycerides of the saturated fatty acids of $C_{10}H_{20}O_2$ to $C_{18}H_{36}O_2$

What is claimed is:

1. Compounds of the general formula I:

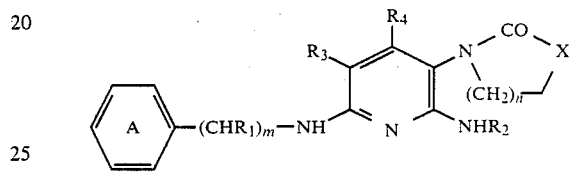

wherein the radicals $R_1$ and $R_2$ are the same or different and represent hydrogen or $C_1$–$C_6$-alkyl, the radicals $R_3$ and $R_4$ are the same or different and represent hydrogen, $C_1$–$C_6$-alkyl, hydroxy, $C_1$–$C_6$-alkoxy, $C_2$–$C_6$-alkanoyloxy, halogen or $C_2$–$C_6$-alkanoyl, X is oxygen, sulphur or the group —$NR_5$ and $R_5$ is hydrogen, $C_1$–$C_6$-alkyl, $C_2$–$C_6$-alkanoyl or benzoyl, m and n in each case may represent the integers 1, 2 or 3 and the phenyl radical A is unsubstituted or is substituted by halogen, nitro, $C_1$–$C_6$-alkyl, trifluoromethyl, $C_3$–$C_7$-cycloalkyl, hydroxy, $C_1$–$C_6$-alkoxy, $C_2$–$C_6$-alkanoyloxy, amino, $C_1$–$C_6$-alkylamino, di-$C_1$–$C_6$-alkylamino, $C_2$–$C_6$-alkanoylamino, CN, carboxy, $C_1$–$C_6$-alkoxycarbonyl, phenyl, $C_1$–$C_6$-alkylphenyl or trifluoromethylphenyl, their pyridine-N-oxides or a physiologically acceptable salt thereof.

2. A pharmaceutical composition consisting of an effective amount of a compound as set forth in claim 1 and at least one pharmaceutically acceptable carrier, diluting agent or auxiliary substances.

3. A method of producing an anti-epileptic effect which comprises administering an anti-epileptically effective amount of a compound as set forth in claim 1.

* * * * *